United States Patent
Ito et al.

(10) Patent No.: US 6,805,887 B2
(45) Date of Patent: Oct. 19, 2004

(54) SUPEROXIDE SCAVENGER AND BEVERAGE CONTAINING SUCH

(75) Inventors: Eizo Ito, Tokyo (JP); Naoki Ito, Tokyo (JP)

(73) Assignee: Shinei Fermentec Corporation, Tokyo (JP)

( * ) Notice: Subject to any disclaimer, the term of this patent is extended or adjusted under 35 U.S.C. 154(b) by 0 days.

(21) Appl. No.: 09/929,066

(22) Filed: Aug. 15, 2001

(65) Prior Publication Data

US 2003/0035858 A1 Feb. 20, 2003

(51) Int. Cl.⁷ .............................. A23L 1/202; A23L 2/00
(52) U.S. Cl. ........................... 426/44; 426/46; 426/598
(58) Field of Search ............................... 426/46, 44, 18, 426/27, 29, 52, 590, 592, 598; 424/115, 195.1, 757

(56) References Cited

U.S. PATENT DOCUMENTS

| | | |
|---|---|---|
| 3,998,761 A | 12/1976 | Gary et al. |
| 4,194,018 A * | 3/1980 | Hodel et al. .............. 426/580 |
| 4,232,122 A | 11/1980 | Zilliken |
| 5,006,337 A | 4/1991 | Motitschke et al. |
| 5,753,640 A | 5/1998 | Araneo et al. |
| 5,824,702 A | 10/1998 | Wei |
| 6,020,367 A | 2/2000 | Duffy et al. |

FOREIGN PATENT DOCUMENTS

| | | | |
|---|---|---|---|
| CN | 1123833 | * | 6/1996 |
| JP | 81-009902 | * | 3/1981 |
| JP | 57-125669 | * | 8/1982 |
| JP | 58-152458 | * | 9/1983 |
| JP | 59-6856 | * | 1/1984 |
| JP | 1-231865 | * | 9/1989 |

* cited by examiner

*Primary Examiner*—Keith Hendricks
(74) *Attorney, Agent, or Firm*—Sughrue Mion, PLLC

(57) ABSTRACT

The present invention provides a superoxide scavenger comprising a desirable material which is different from any conventional unstable superoxide dismutase and is available at a low cost, and the present invention also provides a beverage containing such a superoxide scavenger. The superoxide scavenger and beverage of the present invention comprise a composition extracted from a specific liquid. This specific liquid is prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid.

4 Claims, No Drawings

SUPEROXIDE SCAVENGER AND BEVERAGE CONTAINING SUCH

FIELD OF THE INVENTION

The present invention relates to a superoxide scavenger and a beverage containing such a superoxide scavenger.

BACKGROUND OF THE INVENTION

It is known that superoxide, or free radical $O_2^-$ arising from the one-electron reduction of oxygen molecule, acts as an important protective factor in the body. For example, once the body is invaded by undesirable bacteria, virus, foreign matters or the like, phagocytes such as neutrophils, monocytes and macrophages are activated to exhibit dynamic functions such as migration and phagocytosis. Then, lysozomal enzyme and superoxide are resultingly yield and secreted to get involved directly or indirectly with the lysis and sterilization actions of the phagocytes, which allows the body to be protected from the invading foreign adversary.

Conversely, the excessive presence of the superoxide in the body causes various tissue disorders. The superoxide is generated in the body generally at the rate of 1% or less of oxygen absorbed into the body through respiration, and the generated superoxide is successively scavenged by the catalytic action of superoxide dismutase (SOD) contained in cells. However, if enzymatic actions are degraded as in an aged body, high concentration of the superoxide will be exhibited due to insufficient scavenging function. This leads to tissue disorders such as articular rheumatism or Behcet's Syndrome, or another symptoms arising from superoxide or lipoperoxide generated by the superoxide, such as myocardial infarction, cerebral apoplexy, cataract, blotches, freckles, wrinkles, diabetes, arterial sclerosis, stiff neck, or feeling of cold.

For example, some publications including Japan Patent No. 2667959 propose a cosmetic containing superoxide dismutase. Unfortunately, any cosmetic containing the superoxide dismutase has not been commercially successful because such an enzyme is subjected to deactivation resulting from its instability to heat and is extremely expensive.

An approach for exploring a suitable material having the action of scavenging superoxide other than the superoxide dismutase is described in Japanese Patent Laid-Open Publication No. Sho 64-50877, in which baicalein contained in Scutellaria root is used. However, only a small amount of baicalein is contained in Scutellaria root. Thus, even if a sufficient amount of baicalein is successively extracted, an overdear product will be provided.

SUMMARY OF THE INVENTION

In view of the aforementioned problems, it is therefore an object of the present invention to provide a superoxide scavenger comprising a desirable material which is different from any conventional unstable superoxide dismutase and is available at a low cost.

It is another object of the present invention to provide a beverage containing such a superoxide scavenger.

In order to achieve the above objects, according to a first aspect of the present invention, there is provided a superoxide scavenger comprising a composition extracted from a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid. Preferably, a bean is used as the grain.

According to a second aspect of the present invention, there is provided a beverage containing the aforementioned superoxide scavenger.

According to a third aspect of the present invention, there is provided a beverage containing a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid. Preferably, a bean is used as the grain.

The superoxide scavenger of the present invention can be stably remained even under a temperature of 80° C. or more. Further, using grains as a main ingredient allows the superoxide scavenger to be provided at a lower cost than that of any other conventional superoxide scavengers.

Other features and advantages of the present invention will be apparent from the following description.

DESCRIPTION OF THE PREFERRED EMBODIMENTS

A superoxide scavenger of the present invention comprises a composition extracted from a specific liquid prepared by: boiling a grain with a liquid to obtain a grain liquor; cooling the obtained grain liquor; adding a yeast into the cooled grain liquor; leaving the grain liquor with the yeast while supplying oxygen thereto; and sterilizing the resulting liquid by heating to obtain the specific liquid.

It is believed that the superoxide scavenger of the present invention scavenges superoxide based on the reaction of $2O_2^- + 2H^+ \rightarrow H_2O_2 + O_2$. However, it has not been elucidated that what kind of plant extract in the ingredient could scavenge superoxide.

In manufacturing the superoxide scavenger of the present invention, a suitable grain may include bean, rice, wheat, corn, barnyardgrass, millet or the like. Preferably, a suitable bean includes soy bean, butter bean, red bean, peanut, fava bean, pea, horsebean, cowpea or the like. In order to obtain the grain liquor, 1 to 20 parts of water by weight is first added to 1 part of at least one selected grain. Then, the grain with water is boiled for 30 minutes or more, preferably for 30 minutes to 5 hours. The resulting liquid or hot grain liquor is naturally cooled or self-cooled and then the cooled liquid is filtered to obtain a desired initial grain liquor.

A suitable amount of yeast is added to the initial grain liquor, and the grain liquor with the yeast is left for about 1 to 6 months while supplying oxygen thereto. Preferably, suitable yeast includes any yeast belonging to Saccharomyes, such as beer yeast, wine yeast, sake yeast, or baker's yeast.

In a preferred embodiment, about 10 ml of the initial grain liquor may be first poured into a test tube at room temperature. Then, the yeast may be added into this liquor, and the liquor with the yeast may be left for 1 to 10 days to obtain a first intermediate liquid. Then, 100 ml of the initial grain liquor may be poured into a flask, and the first intermediate liquid may be added into this liquor. The liquor with the first intermediate liquid may be left for 1 to 10 days to obtain a second intermediate liquid. Then, 100 litters of the initial grain liquor may be poured into a tank, and the second intermediate liquid may be added into this liquor, followed by leaving the liquor with the second intermediate liquid for about 1 to 6 months to obtain a stock solution of superoxide scavenger.

The resulting stock solution of superoxide scavenger is sterilized by heating at about 70 to 130° C. for about 2 seconds to 60 minutes. While this sterilized stock solution of superoxide scavenger can be used as a superoxide scavenger as—is, it may be concentrated and further dried under a reduced pressure to use as a dried extract, if necessary.

Preferably, a beverage, such as a soft drink, of the present invention contains about 1 to 10% by weight of the stock solution of superoxide scavenger, in particular, about 5 to 10% by weight of the stock solution of superoxide scavenger.

EXAMPLE

In manufacturing the superoxide scavenger of the present invention, soybean was selected from beans as the grain. First, 600 g of soybeans were immersed in 300 litters of water, and the soybeans with water were left for 10 hours. Then, 100 litters of water was further added to the soybeans with water, and the beans with the increased water were boiled in a pan for 5 hours. Then, the boiled beans and water were naturally cooled or self-cooled. Then, the soybeans were removed to obtain an initial liquor of about 200 litters.

10 ml of the initial liquor was poured in to a test tube, and a suitable amount of sake yeast was added into the liquor. Then, the liquor with the sake yeast was left at room temperature for 2 days to obtain a first intermediate liquid. In the course of this operation, the liquor with the sake yeast was agitated at intervals to supply oxygen thereto.

Then, 100 ml of the initial liquor was poured into a flask, and the first intermediate liquid was added into this liquor. The liquor with the first intermediate liquid was left at room temperature for 2 days to obtain a second intermediate liquid. In the course of this operation, the liquor with the first intermediate liquid was also agitated at intervals to provide oxygen thereto. Then, the obtained second intermediate liquid was poured into the remaining initial liquor, and this liquor with the second intermediate liquid was left for 1 months. In the course of this operation, the liquor with the second intermediate liquid was also agitated at intervals to provide oxygen thereto.

According to the food heat-sterilization process defined by the Public Health Department Regulations, the obtained liquid was sterilized by heating at 85° C. for 30 minutes to obtain a stock solution of superoxide scavenger of the present invention. Using the obtained the stock solution of superoxide scavenger, a superoxide scavenging activity was determined as described below.

1. Measuring Method

Superoxide (activated oxygen) was generated by the hypoxanthine-xanthine oxidase system, and each sample to be measured was added into the obtained superoxide. Then, the superoxide scavenging activity (SOSA) for each sample was determined from the signal strength of ESR (electron spin resonance) spectrum obtained by using the spin-trap process. DETAPAC (di-ethylen triamine penta acetic acid) was added to eliminate metallic impurities.

2. Measuring Equipment and Measuring Condition

Using the ESR JES-REIX made by JEOL Ltd., the measurement was carried out under the following condition.
Observation magnetic field: 355.4±5 mT
Microwave output: 8 mV
Magnetic field modulation amplitude: 0.079 mT
Sweep time: 2 min
Microwave frequency: 100 kHz The stock solution of superoxide according to the invention had a SOSA value of 20.1 unit/ml. Up to now, various comparative measurement values of the superoxide scavenging activity have been obtained, such as 0.2 unit/ml for tap water, 3.8 unit/ml for (pH 8.0) ionized alkaline water, 5.7 unit/ml for (pH 9.0) ionized alkaline water, and 3.6 unit/ml for magnetic water. Since the reproducibility of the measurements is ±0.5 unit/ml, it was verified that in the comparison of liquid to liquid, the stock solution of superoxide scavenger of the present invention had a higher superoxide scavenging activity than that of others. While the superoxide dismutase (Cu-Zu type SOD) made by Wako Pure Chemical Industries, Ltd. has a superoxide scavenging activity value of 3000 to 4000 unit/mg, it is not practicable to compare each superoxide scavenging activities of a solid superoxide scavenger, such as the above superoxide dismutase, and a liquid superoxide scavenger, such as the superoxide scavenger of the present invention, at this time.

In terms of the superoxide scavenging activities of the stock solution of superoxide scavenger described above, it can be expected that the superoxide in the body may be adequately scavenged to provide an improve health condition by regularly drinking the beverage containing the stock solution of superoxide scavenger or the superoxide scavenger extracted from such a stock solution.

The invention has now been explained with reference to specific embodiments. Other embodiments will be apparent to those of ordinary skill in the art. Therefore, it is not intended that the invention be limited, except as indicated by the appended claims, which form a part of this invention description.

What is claimed is:

1. A superoxide scavenger comprising a composition, wherein said composition is prepared by:
   boiling a bean with a liquid to obtain a bean liquor;
   cooling said obtained bean liquor;
   removing said bean from said cooled bean liquor to obtain an initial bean liquor;
   adding a yeast into said initial bean liquor;
   leaving said initial bean liquor with said yeast while supplying oxygen thereto;
   sterilizing the resulting liquid by heating; and
   concentrating and drying the resulting liquid under a reduced pressure.

2. A superoxide scavenger as defined in claim 1, wherein said bean is a soybean.

3. A beverage containing a superoxide scavenger in which said superoxide scavenger comprises a composition, wherein said composition is prepared by:
   boiling a bean with a liquid to obtain a bean liquor;
   cooling said obtained bean liquor;
   removing said bean from said cooled bean liquor to obtain an initial bean liquor;
   adding a yeast into said initial bean liquor;
   leaving said initial bean liquor with said yeast while supplying oxygen thereto;
   sterilizing the resulting liquid by heating; and
   concentrating and drying the resulting liquid under a reduced pressure.

4. A beverage as defined in claim 3, wherein said bean is a soybean.

* * * * *